US006380364B1

(12) United States Patent
Mueller et al.

(10) Patent No.: US 6,380,364 B1
(45) Date of Patent: Apr. 30, 2002

(54) CHIMERIC BIOTIN-BINDING PAPILLOMAVIRUS PROTEIN

(75) Inventors: Martin Mueller, Heidelberg; John D. Nieland, Martinsried, both of (DE); Markwin P. Velders, Forest Park; W. Martin Kast, Willowbrook, both of IL (US)

(73) Assignee: Loyola University of Chicago, Maywood, IL (US)

( * ) Notice: Subject to any disclaimer, the term of this patent is extended or adjusted under 35 U.S.C. 154(b) by 0 days.

(21) Appl. No.: 09/413,611

(22) Filed: Oct. 6, 1999

Related U.S. Application Data
(60) Provisional application No. 60/109,510, filed on Nov. 23, 1998.

(51) Int. Cl.[7] .......................... C07K 1/00; C07K 14/00; C07K 16/00; C07K 17/00; C12N 7/00
(52) U.S. Cl. ..................................... 530/402; 435/235.1
(58) Field of Search ................................. 530/350, 402; 435/235.1

(56) References Cited

FOREIGN PATENT DOCUMENTS

| WO | WO 94/10323 | 5/1994 |
|---|---|---|
| WO | WO 96/11274 | 4/1996 |
| WO | WO 96/30520 | 10/1996 |
| WO | WO 97/19957 | 6/1997 |
| WO | WO 97/46693 | 12/1997 |

OTHER PUBLICATIONS

Cristiano et al. "Hepatic Gene Therapy: Efficient Gene Delivery and Expression in Primary Hepatocytes Utilizing a Conjugated Adenovirus—DNA Complex" *Proc. Natl Acad Sci USA* vol. 90, pp. 11548–11552 (Dec. 1993).

Feltkamp et al. C.W. "Vaccination with Cytotoxic T Lymphocyte Epitope–containing Peptide Protects Against a Tumor Induced by a Human Papillomavirus Type 16–transformed Cells" *Eur. J. Immunol.* vol. 23, pp. 2242–2249 (1993).

Greenstone et al. "Chimeric Papillomavirus Virus–like Particles Elicit Antitumor Immunity Against the E7 Oncoprotein in an HPV16 Tumor Model" *Proc. Natl Acad Sci USA* vol. 95, pp. 1800–1805 (Feb. 1998).

Hiller, et al. "Studies on the Biotin–binding Site of Avidin" *Biochem. Journal* vol. 278, pp. 573–585 (1991).

Müller et al. "Chimeric Papillomavirus–like Particles" *Virology* vol. 234, pp. 93–111 (1997).

Müller et al. "Papillomavirus Capsid Binding and Uptake by Cells from Different Tissues and Species" *Journal of Virology* vol. 69 No. 2, pp. 948–954 (Feb. 1995).

Saggio et al. "Biotin Binders Selected from a Random Peptide Library Expressed on Phage" *Biochem Journal* vol. 293, pp. 613–616 (1993).

Sano et al. "Recombinant Core Streptavidins" *The Journal of Biological Chemistry* vol. 270 No. 47, pp. 28204–28209 (Nov. 1995).

Zhou et al. "Early Phase in the Infection of Cultured Cells with Papillomavirus Virions" *Virology* vol. 214, pp. 167–176 (1995).

De Bruijn et al., *Virology*, 250, 371–376 (1998).

Schoenberger et al., *Cancer Research*, 58, 3094–3100 (1998).

Toes et al., *The Journal of Immunology*, 160, 4449–4456 (1998).

Marjomaki et al. *Molecular Biology of the Cell*, 7, 2631 (1996).

*Primary Examiner*—Gary L. Kunz
*Assistant Examiner*—Robert S. Landsman
(74) *Attorney, Agent, or Firm*—Leydig, Voit & Mayer, Ltd

(57) ABSTRACT

The present invention provides a chimeric protein including a first domain which includes at least a portion of a papillomavirus L1 or L2 protein and a second domain which includes a biotin-binding polypeptide. The invention also provides papillomaviruses, capsomeres, and VLPs including such chimeric proteins and a method for delivering biotinylated substances to cells using such reagents.

17 Claims, No Drawings

CHIMERIC BIOTIN-BINDING PAPILLOMAVIRUS PROTEIN

CROSS REFERENCE TO RELATED APPLICATIONS

This application claims priority to United States Provisional Patent Application No. 60/109,510, which was filed on Nov. 23, 1998.

STATEMENT AS TO RIGHTS TO INVENTIONS MADE UNDER FEDERALLY SPONSORED RESEARCH AND DEVELOPMENT

This invention was made with support under Grant Number RO1 CA74397 awarded by the U.S. National Institutes of Health. The United States Government may have certain rights in this invention.

TECHNICAL FIELD OF THE INVENTION

This invention relates to a chimeric biotin-binding papillomavirus protein.

BACKGROUND OF THE INVENTION

Papillomavirus are causative agents for several types of epithelial and mucosal diseases. Of particular concern is that certain strains of papillomavirus are associated with genital cancers, cancers of the head and neck, and also rectal cancers (see, e.g., Iwasawa et al., *J. Urol.*, 149, 59–63 (1993); Koutsky et al., *N. Engl. J. Med.*, 327, 1272–78 (1992)). Considerable efforts, therefore, are underway to prevent the spread of this virus by developing a prophylactic vaccine and novel treatments for papillomavirus-induced lesions (see, e.g., Cason et al., *Vaccine*, 11, 603–11 (1993); Crawford, *Cancer Suev.*, 16, 215–29 (1993), Schiller et al., in *Papillomavirus-Like Particles: Basic and Applied Studies* (Lacey, C., ed., 101–12 (Leeds Medical Information, Leeds, U.K., 1996)).

Papillomaviruses are nonenveloped double-stranded DNA viruses about 55 nm in diameter with an approximately 8-kb genome in a nucleohistone core (Baker et al., *Biophys J.* 60, 1445–56 (1991)). The capsids include two viral proteins (L1 and L2) of about 55 kDa and 75 kDa, respectively (Larson et al., *J. Virol.*, 61, 3596–3601 (1987)). L1 is the major capsid protein, and it is arranged in 72 pentameres within the capsid. In fact, L1 has the ability to self-assemble into virus-like particles (VLPs) upon production of the L1 protein in eukaryotic cells (see, e.g., Hagensee et al., *J. Virol.*, 67, 315–22 (1993); Kirnbauer et al., *J. Virol.*, 67, 6929–36 (1993)). The function and position of L2 within the virion are not clear, although the protein is assembled with L1 into VLPs when coexpressed in cells. The ratio of L1 to L2 within VLPs is about 30:1 (Kirnbauer et al., *J. Virol.*, 67, 6929–36 (1993)).

VLPs typically are used for in vitro studies of papillomavirus infection, as opposed to intact papillomavirus (see, e.g., Roden et al., *J. Virol.*, 68, 7260–66 (1994); Volpers et al., *J. Virol.*, 69, 3258–64 (1995)), because of the lack of a suitable in vitro culture system. While it has been suggested that VLPs may prove useful as vectors for targeting drugs, nucleic acids, or other substances to cells subject to papillomavirus infection, they have not proven useful as a vector system. Recently, it has been discovered that chimeric fusion proteins consisting of the amino-terminal portion of the L1 or L2 protein fused to a portion of a non-structural papillomavirus protein are able to assemble into capsomeres and VLPs. VLPs including such chimeric molecules have been demonstrated to elicit an immune response from cells (see, e.g., published international application WO 96/11274; Müller et al., *Virology*, 234, 93–111 (1997); Greenstone et al., *Proc. Nat. Acad. Sci. (USA)*, 95, 1800–05 (1998)). While it is thus possible to use such chimeric capsomeres or VLPs for delivering the non-L1 or L2 portion of such fusion proteins to cells (e.g., as vaccines), the method is of limited utility. For example, such a method does not permit the delivery of nucleic acids or other non-proteinaceous species to cells. Moreover, such a method requires the engineering of a novel chimeric capsid protein for each desired application. In view of the foregoing problems, there exists a need for a vector system able to deliver a wide variety of substances to cells subject to papillomavirus infection.

BRIEF SUMMARY OF THE INVENTION

The present invention provides a chimeric protein including a first domain which includes at least a portion of a papillomavirus L1 or L2 protein and a second domain which includes a biotin-binding polypeptide. The invention also provides papillomaviruses, capsomeres, and VLPs including such chimeric proteins and a method for delivering biotinylated substances to cells using such reagents. These and other advantages of the present invention, as well as additional inventive features, will be apparent from the following detailed description.

DETAILED DESCRIPTION OF THE INVENTION

The first domain of the chimeric protein includes at least a portion of a papillomavirus L1 or L2 protein. The sequence of the L1 and L2 proteins of many papillomaviruses is known, and the chimeric protein can include all or a portion of the L1 or L2 protein from any papillomavirus strain. The second domain includes a biotin-binding polypeptide, and it can be derived from any protein known to bind biotin, many of which are known in the art (see, e.g., Green et al., *Meth. Enzymol.*, 184, 51–67 (1990); Howard et al., *Gene*, 35, 321–31 (1985); Li et al., *J. Biol. Chem.*, 267, 855–63 (1992); Saggio et al., *Biochem. J.*, 293, 613–16 (1993); Hiller et al., *Biochem. J.*, 278, 573–85 (1991)). Examples of proteins from which the biotin-binding domain of the inventive chimeric protein, thus, include avidin, streptavidin, biotin operon repressor and biotin holoenzyme synthase, biotin carboxylase, biotin-binding phage, and the like.

Each domain of the chimeric protein contributes its respective function to the chimeric protein of the present invention. Thus, an L1 domain is able to interact as a native L1 protein (i.e., with either native L1 proteins from the same strain as the chimeric protein is derived or with other chimeric proteins) to form papillomaviruses, capsomeres, or VLPs. The L1 protein can be further modified (e.g., by deleting the residue corresponding to Cys 428 of the wild-type HPV 16 protein) to render it more able to form capsomeres than VLPs. Such modification is preferable in some applications to ensure that the biotin-binding domain is exposed, rather than hidden in the internal region of a VLP. Depending on how the protein is produced, however, an L1 domain can represent wild-type L1 sequence to permit the resulting chimeric protein to assemble into whole papillomaviruses or VLPs. Moreover, an L1 domain includes sequences able to bind receptors present on target cell surfaces. To provide these functions, where the chimeric protein includes an L1 domain, typically it includes at least the amino-terminal portion of the L1 protein. Similarly, where the chimeric protein includes an L2 domain, the L2 domain permits the chimeric protein to be incorporated into VLPs (see, e.g., WO 96/11274; Greenstone et al., supra). Similarly, the domain derived from a biotin-binding protein function as a ligand for biotin, thereby conferring biotin-binding ability to the chimeric protein of the present invention. Importantly, the biotin-binding domain should not be so large so as to inhibit the capsomere-, virus-, or VLP-forming ability of the L1- or L2-derived domain. Thus, where the chimeric protein includes a L1 domain, preferably, the biotin-binding domain is smaller than about 50 amino acids (e.g., smaller than about 30 amino acids), such as about 20 amino acids or smaller. Where the chimeric protein includes an L2 domain, the biotin-binding domain can be (but need not be) somewhat larger, for example, smaller than about 150 amino acids (e.g., smaller than about 100 amino acids), such as about 75 amino acids or smaller.

Chimeric proteins of the present invention can be synthesized using standard direct peptide synthesizing techniques (see, e.g., Bodanszky, *Principles of Peptide Synthesis* (Springer-Verlag, Heidelberg: 1984)), such as via solid-phase synthesis (see, e.g., Merrifield, *J. Am. Chem. Soc.*, 85, 2149–54 (1963); Barany et al., *Int. J. Peptide Protein Res.*, 30, 705–739 (1987); and U.S. Pat. No. 5,424,398). Alternatively, such modified proteins can be chemically crosslinked, and a variety of cross-linking agents are known in the art and widely available (e.g., succinimidyl or male-imidyl cross-linkers). Methods for conjugating peptides and polyamines are also well-known in the art (see, e.g., Staros, *Biochem.*, 21, 3990 (1982)). Alternatively, a DNA fragment encoding the chimeric protein can be subcloned into an appropriate vector using well known molecular genetic techniques. The fragment then is transcribed and the peptide subsequently translated in vitro within a host cell. Any appropriate expression vector (see, e.g., Pouwels et al., *Cloning Vectors: A Labratory Manual* (Elsevior, N.Y.: 1985)) and corresponding suitable host cells can be employed for production of recombinant peptides. Expression hosts include, but are not limited to, bacterial species, mammalian or insect host cell systems including baculovirus systems (e.g., as described by Luckow et al., *Bio/Technology*, 6, 47 (1988)), and established cell lines such 293, COS-7, C127, 3T3, CHO, HeLa, BHK, etc. From such cells, the modified chimeric proteins can be harvested by standard techniques.

As mentioned, by virtue of the L1- or L2-derived domain, the chimeric protein of the present invention preferably is able to be incorporated into papillomaviruses and VLPs. Thus, the present invention provides a papillomavirus or VLP including at least one chimeric protein such as previously described. Preferably, a majority of the L1 or L2 domains in the papillomavirus or VLP are contributed by such chimeric proteins, and it is most preferred for all of the L1 or L2 domains in the papillomavirus or VLP to be contributed by such chimeric proteins. Of course, a papillomavirus or VLP can include some native L1 and/or L2 proteins, or other derivatives of L1 or L2 proteins not binding biotin. By virtue of the biotin-binding domain present on the proteins, the papillomavirus or VLP is able to bind biotin with high affinity.

Because each domain of the chimeric protein contributes its respective function to the chimeric protein, where the chimeric protein includes an L1 domain, the protein is able to form a capsomere. Thus, the present invention provides such a capsomere including at least one chimeric protein such as previously described, particularly one having an L1 domain. Preferably, a majority of the proteins in the capsomere are such chimeric proteins, and it is most preferred for the capsomere to include only such chimeric proteins. By virtue of the biotin-binding domain present on the proteins, the capsomere is able to bind biotin with high affinity.

Capsomeres, papillomavirus, and VLPs including the inventive chimeric proteins can be produced by methods known in the art. Typical methods for producing capsomeres and VLPs involve the expression of at lest a gene encoding L1 proteins within a suitable host cell. Coexpression of the L2 protein permits the L2 protein to be included within the VLP. Once produced within the host cell, the gene products aggregate to form intact viruses, capsomeres, and/or VLPs, which are then isolated from the cell and purified (see, e.g., Müller et al., *Virology*, 234, 93–111 (1997)). Such standard methods are equally applicable to papillomaviruses, capsomeres, and VLPs incorporating the chimeric proteins of the present invention. However, the presence of the biotin-binding domain affords an additional method of purifying such viruses, capsomeres and VLPs using a biotin in accordance with standard protocols (e.g., on an affinity column or other suitable support).

Because the L1- or L2-derived domains of the inventive chimeric proteins retain the ability to bind cellular receptors, viruses, capsomeres, and VLPs incorporating such chimeric proteins can be employed to deliver biotinylated substances to cells, particularly cells normally infected by papillomaviruses. Thus, an aspect of the present invention is a method for delivering a biotinylated compound to a cell. The method involves first forming a complex comprising the biotinylated substance and a papillomavirus, capsomere, or VLP including a chimeric protein as herein described. Subsequently, the complex is exposed to the cell under conditions sufficient for the complex to bind the cell.

The cell is any cell for which papillomaviruses are normally tropic. In this regard, the method can be employed to deliver the biotinylated substance to cells either in vitro or in vivo, depending on the desired application of the method. Cell binding is mediated, at least primarily, via by the ligand-substrate interaction between the L1 proteins (e.g., any native L1 proteins as well as chimeric proteins containing L1 domains) comprising the papillomavirus, capsomere, or VLP. Thus, the strain of papillomavirus from which the L1 domain of the chimeric protein is derived (or other L1 proteins or derivatives present in the complex) can be selected so as to target the biotinylated substance to a given cell type.

The method can be employed to deliver any desired substance to the cells of interest, provided that the substance can be biotinylated (e.g., conjugated to a biotin-like molecule). For example, the substance can include a protein, a polynucleic acid, a drug, etc. Some substances function as markers for identifying cells to which the complex has been delivered. Thus, for use as a vaccine, the substance can be or comprise a viral antigen (e.g., a papillomavirus E2 or E7 protein). In other applications, the substance can be or comprise a compound that exerts a biological effect on the infected cells. For example, because the complex is targeted to cells for which papillomaviruses exhibit tropism, the substance can exert a biological effect on papillomavirus-infected cells or cells subject to infection. Thus, for treating tumors (e.g., cervical or penile cancers), warts, or other papillomavirus-related lesions, the substance can be a medicament, cytotoxin, chemotherapeutic agent, radioactive agent, etc. In other embodiments, the substance can be a nucleic acid including a gene encoding a bioactive molecule. In such circumstances, the complex delivers the nucleic acid to the infected cells such that the cells internalize it and can express the gene to produce the bioactive molecule. For combating tumors associated with papillomavirus infection, such a gene can encode a cytokine (e.g., tumor necrosis factor (TNF), TGF-α, TGF-β, interleukins (IL) such as IL-1, L-2, IL-3, etc., GM-CSF, G-CSF, M-CSF, co-stimulatory factor B7, etc.), a protein that promotes cell death or an enzyme that converts a prodrug into a cytotoxin (e.g., HSV-tk, cytosine deaminase, xanthine/guanine phosphoribosyl transferase, cytochrome p450 2B1, etc.). In other applications, the gene can encode a viral antigen to function in an immunotherapeutic protocol (e.g., a papillomavirus E2 or E7 antigen). Still other bioactive molecules are RNA species having sequences antisense to portions of papillomavirus genes (e.g., the genes encoding L1, L2).

While many such substances for delivery to cells in accordance with the inventive method can be obtained commercially as biotinylated compounds, other substances not available as biotinylated preparations can be conjugated to biotin before use in the inventive method using standard techniques (see, e.g., Parmley et al., *Gene*, 73, 305–18 (1988)). Once biotinylated, the substance to be delivered to the cell is exposed to a papillomavirus, capsomere, or VLP including a chimeric protein under conditions for the two to form a complex. Such a complex is formed by virtue of the high affinity ligand-substrate interaction between the biotin-binding portion of the chimeric protein(s) comprising the papillomavirus, capsomere, or VLP. The stoichiometric ratio of the number of biotinylated substance particles to the capsomere or VLP will vary depending on the proportion of chimeric proteins of the type herein described within the papillomavirus, capsomere, or VLP. The interaction of biotin with its ligands is well-known, and the complex can be formed under any suitable condition which will permit such interaction.

In addition to including the biotinylated substance and the papillomavirus, capsomere, or VLP including a chimeric protein as herein described, the complex can also include other constituents (e.g., one or more proteins, polynucleic acids, lipids, drugs, etc.). For example, incorporating lipids into the complex (e.g., in the form of liposomes) enhances cellular uptake of many types of pharmacologically active agents, especially nucleic acids (see, e.g., Innes et al., *J. Virol.*, 64, 957–61 (1990); Morishaita et al., *Hypertension*, 21, 894–99 (1993); U.S. Pat. No. 5,635,380). Where a liposome is employed in the complex, and where the biotinylated substance includes a polynucleic acid, preferably the liposome contains cationic lipids, but it can, of course, contain neutral lipids as well. Preferred cationic lipids include LIPOFECTIN (DOTMA) (Gibco BRL), LIPOFECTMINE (Gibco BRL), and DOTAP (Boeringer-Mannheim), and others are known in the art (see, e.g., U.S. Pat. No. 5,736,392).

Once formed, the complex is exposed to the cell under conditions sufficient for the complex to bind the cell. The biotinylated substance is thus brought into proximity to, and delivered to, the cell. In some instances, the substance is internalized into the cell, while in other instances, it remains in contact (either transiently or long-term) with the exterior of the cell where it exerts its effect.

As mentioned, the inventive method can be employed to deliver the substance to cells either in vivo or in vitro. To facilitate the application of the method in vivo, the invention provides a pharmaceutical composition comprising a complex as herein described and a pharmaceutically-acceptable carrier. Such compositions can be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention can be formulated in a conventional manner using one or more pharmacologically or physiologically acceptable carriers comprising excipients, as well as optional auxiliaries which facilitate processing of the active compounds into preparations which can be used pharmaceutically. Proper formulation is dependent upon the route of administration chosen. Thus, for injection, the active ingredient can be formulated in aqueous solutions, preferably in physiologically compatible buffers. For trausmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. For administration by inhalation, the active ingredient is conveniently delivered in the form of an aerosol spray presentation from pressurized packs or a nebuliser, with the use of a suitable propellant. The active ingredient can be formulated for parenteral administration by injection, e.g., by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

While it is believed that one of skill in the art is fully able to practice the present invention after reading the foregoing detailed description, the following examples are set forth to further illustrate some of its features. In particular, these examples detail several chimeric proteins, each including a first domain which includes at least a portion of a papillomavirus L1 protein and a second domain which includes a biotin-binding polypeptide. The examples also demonstrate that such proteins can be employed as described above to deliver biotinylated substances to cells. As these examples are included for purely illustrative purposes, they should not be construed to limit the scope of the invention in any respect.

The procedures employed in these examples, such as vector construction (including DNA extraction, isolation, restriction digestion, ligation, sequencing etc.), PCR, cell culture (including antibiotic selection), transfection of cells, protein assays (Western blotting, immunoprecipitation, immunofluorescence, ELISA, Wehi assays, etc.), etc. are techniques routinely performed by those of skill in the art (see generally Sambrook et al., *Molecular Cloning, A Laboratory Manual*, Cold Spring Harbor Laboratory, Cold Spring Harbor, N.Y. (1989)). Accordingly, in the interest of brevity, such basic elementary experimental protocols are not discussed in detail.

EXAMPLE 1

This Example demonstrates the construction of two chimeric biotin-binding papillomavirus L1 proteins.

A first mutation at cystein 428 was introduced into the human papillomavirus 16 L1 gene to prevent assembly of VLPs while allowing the production of capsomeres at high efficiencies. This L1-derived sequence was used to create control protein lacking the biotin-binding domain (the "152" protein).

To create the chimeric proteins, the mutant L1-derived sequence was fused at the carboxyl-terminus in frame and in place of the terminal 69 base pairs to either of two sequences encoding a biotin-binding peptide (SEQ ID NOS:1 and 3). The resultant genes encode chimeric L1-derived proteins (the "168" and "169" proteins, respectively), each including a first domain derived from the L1 protein and a second domain which includes a biotin-binding polypeptide. The full length sequences of these genes, and the resulting proteins, are set forth in SEQ ID NOS:5–8).

To produce capsomeres, the genes were subcloned into a baculovirus expression vector system and introduced into insect cells. Protein produced by the host insect cells was purified by ultra-centrifugation and analyzed as described below.

EXAMPLE 2

This example demonstrates that the capsomeres including chimeric biotin-binding papillomavirus L1 proteins are able to bind biotin.

Protein produced from the insect cells described in Example 1 was subjected to analysis by Western-blot and ELISA. Western analysis revealed that all three resultant proteins were recognized by antibodies directed against the L1 protein. However, only the 168 and 169 proteins reacted positively to biotin in an antigen-capture ELISA using biotinylated horseradish peroxidase. These results indicate that the chimeric proteins, and not the control 152 protein, bind biotin, but that all are recognizable HPV L1-derivatives.

EXAMPLE 3

This example demonstrates that the capsomeres including chimeric biotin-binding papillomavirus L1 proteins are able to interact with the surface of cells.

Cultured P815 cells were exposed to either the control 152 capsomeres or the chimeric 168 or 169 capsomeres. The cells were subsequently probed with biotin-FITC conjugates and analyzed by fluorescent activated cell sorting (FACS).

The results indicated that the 168 and 169 capsomeres were able to bind the cell surface and interact with biotinylated ligands. In contrast, the 152 capsomeres were able to bind the cell surfaces, but they did not react positively when exposed to the FITC-conjugated biotin. These results indicate that the chimeric proteins can form capsomeres that are able to interact with both the surface of papillomavirus-susceptible cells and to bind biotinylated ligands.

EXAMPLE 4

This example demonstrates the ability of capsomeres including chimeric biotin-binding papillomavirus L1 proteins to introduce protein into cells.

In standard phosphate-buffered saline (PBS), three concentrations (10 nM, 100 nM and 1000 nM of biotinylated papillomavirus E7 peptide were incubated with either the 152 capsomeres or the 169 capsomeres at 37° C. for two hours. Subsequently, C57 Bl/6 splenocytes were added to the particles. These preparations, as well as a preparation of the biotinylated E7 polypeptide alone, were introduced into the wells of tissue culture plates into which 10,000 F anti C3 T cells (an E7-specific CTL clone) had been cultured The following day, the supernatants were harvested and assayed for the presence of TNFα via a standard Wehi assay. The presence of TNFα was indicative of internalzation and processing of the E7 protein.

The results of this assay revealed that TNFα concentration was not markedly changed upon exposure of the cells to any concentration of E7 protein alone or the preparation of the biotinylated E7 protein and the 152 capsomeres. However, TNFα concentration was markedly elevated upon exposure of the cells to all concentrations of the preparation of the biotinylated E7 protein and the 169 capsomeres. The results indicate that the capsomeres including chimeric biotin-binding papillomavirus L1 proteins were able to mediate the uptake and processing of the protein by the cells.

EXAMPLE 5

This example demonstrates the ability of capsomeres including chimeric biotin-binding papillomavirus L1 proteins to introduce genetic material into cells.

A biotinylated plasmid containing a gene encoding green-fluorescent-peptide is incubated with either the 152 capsomeres or the 169 capsomeres as described above. These preparations, as well as a preparation of the biotinylated plasmid alone, are introduced into the wells of tissue culture plates containing papillomavirus-susceptible cells. After two hours, the cells are rinsed and incubated. Following the incubation, the cells are observed for fluorescence staining. Greater fluorescence in the population exposed to the 169/GAP complex indicates that capsomeres including chimeric biotin-binding papillomavirus L1 proteins are able to mediate the uptake and processing of the genetic vectors by the cells.

All of the references cited herein, including patents, patent applications, and publications, are hereby incorporated in their entireties by reference.

While the present invention has been described with an emphasis upon preferred embodiments and illustrative examples, it will be obvious to those of ordinary skill in the art that variations of the preferred embodiments may be used and that the present invention can be practiced otherwise than as specifically described herein. Accordingly, the present invention includes all modifications encompassed within the spirit and scope of the invention as defined by the following claims.

What is claimed is:

1. A chimeric protein including a first domain which comprises at least a portion of a papillomavirus L1 or L2 protein and a second domain which comprises a biotin-binding polypeptide, wherein said portion can integrate into a capsomere, a virus-like particle (VLP), or papillomavirus.

2. The chimeric protein of claim 1, wherein said second domain is derived from avidin, streptavidin, biotin operon repressor and biotin holoenzyme synthase, biotin carboxylase, or biotin-binding phage.

3. The chimeric protein of claim 1, wherein said second domain comprises SEQ ID NOS:1 or 3.

4. The chimeric protein of claim 1, wherein said first domain comprises the amino-terminal portion of said papillomavirus L1 protein.

5. The chimeric protein of claim 1, wherein the first domain comprises at least a portion of a papillomavirus L1 protein.

6. The chimeric protein of claim 1, wherein the first domain comprises at least a portion of a papillomavirus L2 protein.

7. The chimeric protein of claim 1, wherein the second domain is derived from avidin.

8. The chimeric protein of claim 1, wherein the second domain is derived from streptavidin.

9. The chimeric protein of claim 1, wherein the second domain is derived from biotin operon repressor and biotin holoenzyme synthase.

10. The chimeric protein of claim 1, wherein the second domain is derived from biotin carboxylase.

11. The chimeric protein of claim 1, wherein the second domain is derived from biotin-binding phage.

12. The chimeric protein of claim 1, wherein the biotin-binding polypeptide comprises a domain consisting essentially of the biotin-binding domain of avidin, streptavidin, biotin operon repressor and biotin holoenzyme synthase, biotin carboxylase, or biotin-binding phage.

13. The chimeric protein of claim 1, wherein the biotin-binding polypeptide comprises a domain consisting essentially of the biotin-binding domain of avidin.

14. The chimeric protein of claim 1, wherein the biotin-binding polypeptide comprises a domain consisting essentially of the biotin-binding domain of of streptavidin.

15. The chimeric protein of claim 1, wherein the biotin-binding polypeptide comprises a domain consisting essentially of the biotin-binding domain of biotin operon repressor and biotin holoenzyme synthase.

16. The chimeric protein of claim 1, wherein the biotin-binding polypeptide comprises a domain consisting essentially of the biotin-binding domain of biotin carboxylase.

17. The chimeric protein of claim 1, wherein the biotin-binding polypeptide comprises a domain consisting essentially of the biotin-binding domain of a biotin-binding phage.

* * * * *

SEQUENCE LISTING

```
<160> NUMBER OF SEQ ID NOS:  8

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence:Biotin I
      sequence with Gly-Gly-Gly hinge
<221> NAME/KEY: CDS
<222> LOCATION: (1)..(42)
```

<400> SEQUENCE: 1

```
ggc ggc ggc tgc tcc tgg gcc ccc ccc ttc aag gcc tcc tgc taa        45
Gly Gly Gly Cys Ser Trp Ala Pro Pro Phe Lys Ala Ser Cys
 1               5                  10
```

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence:Biotin I
      sequence with Gly-Gly-Gly hinge

<400> SEQUENCE: 2

```
Gly Gly Gly Cys Ser Trp Ala Pro Pro Phe Lys Ala Ser Cys
 1               5                  10
```

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence:Biotin II
      sequence with Gly-Gly-Gly hinge
<221> NAME/KEY: CDS
<222> LOCATION: (1)..(48)

<400> SEQUENCE: 3

```
ggc ggc ggc cgc ggc gag ttc acc ggc acc tac atc acc gcc gtg acc   48
Gly Gly Gly Arg Gly Glu Phe Thr Gly Thr Tyr Ile Thr Ala Val Thr
 1               5                  10                  15 taa                                                                51
```

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence:Biotin II
      sequence with Gly-Gly-Gly hinge

<400> SEQUENCE: 4

```
Gly Gly Gly Arg Gly Glu Phe Thr Gly Thr Tyr Ile Thr Ala Val Thr
 1               5                  10                  15
```

<210> SEQ ID NO 5
<211> LENGTH: 1494
<212> TYPE: DNA
<213> ORGANISM: Artificial Sequence
<220> FEATURE:
<223> OTHER INFORMATION: Description of Artificial Sequence:
      biotin-binding papillomavirus protein 168
<221> NAME/KEY: CDS
<222> LOCATION: (1)..(1491)

<400> SEQUENCE: 5

```
atg tct ctt tgg ctg cct agt gag gcc act gtc tac ttg cct cct gtc   48
Met Ser Leu Trp Leu Pro Ser Glu Ala Thr Val Tyr Leu Pro Pro Val
 1               5                  10                  15 cca gta tct aag gtt gta agc acg gat gaa tat gtt gca cgc aca aac   96
Pro Val Ser Lys Val Val Ser Thr Asp Glu Tyr Val Ala Arg Thr Asn
                20                  25                  30 ata tat tat cat gca gga aca tcc aga cta ctt gca gtt gga cat ccc  144
Ile Tyr Tyr His Ala Gly Thr Ser Arg Leu Leu Ala Val Gly His Pro
            35                  40                  45
```

```
tat ttt cct att aaa aaa cct aac aat aac aaa ata tta gtt cct aaa        192
Tyr Phe Pro Ile Lys Lys Pro Asn Asn Asn Lys Ile Leu Val Pro Lys
 50              55                  60 gta tca gga tta caa tac agg gta ttt aga ata cat tta cct gac ccc        240
Val Ser Gly Leu Gln Tyr Arg Val Phe Arg Ile His Leu Pro Asp Pro
 65              70                  75                  80 aat aag ttt ggt ttt cct gac acc tca ttt tat aat cca gat aca cag        288
Asn Lys Phe Gly Phe Pro Asp Thr Ser Phe Tyr Asn Pro Asp Thr Gln
                 85                  90                  95 cgg ctg gtt tgg gcc tgt gta ggt gtt gag gta ggt cgt ggt cag cca        336
Arg Leu Val Trp Ala Cys Val Gly Val Glu Val Gly Arg Gly Gln Pro
            100                 105                 110 tta ggt gtg ggc att agt ggc cat cct tta tta aat aaa ttg gat gac        384
Leu Gly Val Gly Ile Ser Gly His Pro Leu Leu Asn Lys Leu Asp Asp
        115                 120                 125 aca gaa aat gct agt gct tat gca gca aat gca ggt gtg gat aat aga        432
Thr Glu Asn Ala Ser Ala Tyr Ala Ala Asn Ala Gly Val Asp Asn Arg
    130                 135                 140 gaa tgt ata tct atg gat tac aaa caa aca caa ttg tgt tta att ggt        480
Glu Cys Ile Ser Met Asp Tyr Lys Gln Thr Gln Leu Cys Leu Ile Gly
145                 150                 155                 160 tgc aaa cca cct ata ggg gaa cac tgg ggc aaa gga tcc cca tgt acc        528
Cys Lys Pro Pro Ile Gly Glu His Trp Gly Lys Gly Ser Pro Cys Thr
                165                 170                 175 aat gtt gca gta aat cca ggt gat tgt cca cca tta gag tta ata aac        576
Asn Val Ala Val Asn Pro Gly Asp Cys Pro Pro Leu Glu Leu Ile Asn
            180                 185                 190 aca gtt att cag gat ggt gat atg gtt gat act ggc ttt ggt gct atg        624
Thr Val Ile Gln Asp Gly Asp Met Val Asp Thr Gly Phe Gly Ala Met
        195                 200                 205 gac ttt act aca tta cag gct aac aaa agt gaa gtt cca ctg gat att        672
Asp Phe Thr Thr Leu Gln Ala Asn Lys Ser Glu Val Pro Leu Asp Ile
    210                 215                 220 tgt aca tct att tgc aaa tat cca gat tat att aaa atg gtg tca gaa        720
Cys Thr Ser Ile Cys Lys Tyr Pro Asp Tyr Ile Lys Met Val Ser Glu
225                 230                 235                 240 cca tat ggc gac agc tta ttt ttt tat tta cga agg gaa caa atg ttt        768
Pro Tyr Gly Asp Ser Leu Phe Phe Tyr Leu Arg Arg Glu Gln Met Phe
                245                 250                 255 gtt aga cat tta ttt aat agg gct ggt gct gtt ggt gaa aat gta cca        816
Val Arg His Leu Phe Asn Arg Ala Gly Ala Val Gly Glu Asn Val Pro
            260                 265                 270 gac gat tta tac att aaa ggc tct ggg tct act gca aat tta gcc agt        864
Asp Asp Leu Tyr Ile Lys Gly Ser Gly Ser Thr Ala Asn Leu Ala Ser
        275                 280                 285 tca aat tat ttt cct aca cct agt ggt tct atg gtt acc tct gat gcc        912
Ser Asn Tyr Phe Pro Thr Pro Ser Gly Ser Met Val Thr Ser Asp Ala
    290                 295                 300 caa ata ttc aat aaa cct tat tgg tta caa cga gca cag ggc cac aat        960
Gln Ile Phe Asn Lys Pro Tyr Trp Leu Gln Arg Ala Gln Gly His Asn
305                 310                 315                 320 aat ggc att tgt tgg ggt aac caa cta ttt gtt act gtt gtt gat act       1008
Asn Gly Ile Cys Trp Gly Asn Gln Leu Phe Val Thr Val Val Asp Thr
                325                 330                 335 aca cgc agt aca aat atg tca tta tgt gct gcc ata tct act tca gaa       1056
Thr Arg Ser Thr Asn Met Ser Leu Cys Ala Ala Ile Ser Thr Ser Glu
            340                 345                 350 act aca tat aaa aat act aac ttt aag gag tac cta cga cat ggg gag       1104
Thr Thr Tyr Lys Asn Thr Asn Phe Lys Glu Tyr Leu Arg His Gly Glu
        355                 360                 365
```

-continued

```
gaa tat gat tta cag ttt att ttt caa ctg tgc aaa ata acc tta act     1152
Glu Tyr Asp Leu Gln Phe Ile Phe Gln Leu Cys Lys Ile Thr Leu Thr
    370                 375                 380 gca gac gtt atg aca tac ata cat tct atg aat tcc act att ttg gag     1200
Ala Asp Val Met Thr Tyr Ile His Ser Met Asn Ser Thr Ile Leu Glu
385                 390                 395                 400 gac tgg aat ttt ggt cta caa cct ccc cca gga ggc aca cta gaa gat     1248
Asp Trp Asn Phe Gly Leu Gln Pro Pro Pro Gly Gly Thr Leu Glu Asp
                405                 410                 415 act tat agg ttt gta acc tcc cag gca att gct agt caa aaa cat aca     1296
Thr Tyr Arg Phe Val Thr Ser Gln Ala Ile Ala Ser Gln Lys His Thr
            420                 425                 430 cct cca gca cct aaa gaa gat ccc ctt aaa aaa tac act ttt tgg gaa     1344
Pro Pro Ala Pro Lys Glu Asp Pro Leu Lys Lys Tyr Thr Phe Trp Glu
        435                 440                 445 gta aat tta aag gaa aag ttt tct gca gac cta gat cag ttt cct tta     1392
Val Asn Leu Lys Glu Lys Phe Ser Ala Asp Leu Asp Gln Phe Pro Leu
    450                 455                 460 gga cgc aaa ttt tta cta caa gca gga ttg aag gcc aaa cca aaa ttt     1440
Gly Arg Lys Phe Leu Leu Gln Ala Gly Leu Lys Ala Lys Pro Lys Phe
465                 470                 475                 480 aca tta gga ggc ggc ggc tgc tcc tgg gcc ccc ccc ttc aag gcc tcc     1488
Thr Leu Gly Gly Gly Gly Cys Ser Trp Ala Pro Pro Phe Lys Ala Ser
                485                 490                 495 tgc taa                                                             1494
Cys

<210> SEQ ID NO 6
<211> LENGTH: 497
<212> TYPE: PRT
<213> ORGANISM: Artificial Sequence
<220> FEATURE:
<223> OTHER INFORMATION: Description of Artificial Sequence:
      biotin-binding papillomavirus protein 168

<400> SEQUENCE: 6

Met Ser Leu Trp Leu Pro Ser Glu Ala Thr Val Tyr Leu Pro Pro Val
  1               5                  10                  15

Pro Val Ser Lys Val Val Ser Thr Asp Glu Tyr Val Ala Arg Thr Asn
             20                  25                  30

Ile Tyr Tyr His Ala Gly Thr Ser Arg Leu Leu Ala Val Gly His Pro
         35                  40                  45

Tyr Phe Pro Ile Lys Lys Pro Asn Asn Asn Lys Ile Leu Val Pro Lys
     50                  55                  60

Val Ser Gly Leu Gln Tyr Arg Val Phe Arg Ile His Leu Pro Asp Pro
 65                  70                  75                  80

Asn Lys Phe Gly Phe Pro Asp Thr Ser Phe Tyr Asn Pro Asp Thr Gln
                 85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175
```

```
Asn Val Ala Val Asn Pro Gly Asp Cys Pro Pro Leu Glu Leu Ile Asn
            180                 185                 190
Thr Val Ile Gln Asp Gly Asp Met Val Asp Thr Gly Phe Gly Ala Met
            195                 200                 205
Asp Phe Thr Thr Leu Gln Ala Asn Lys Ser Glu Val Pro Leu Asp Ile
            210                 215                 220
Cys Thr Ser Ile Cys Lys Tyr Pro Asp Tyr Ile Lys Met Val Ser Glu
225                 230                 235                 240
Pro Tyr Gly Asp Ser Leu Phe Phe Tyr Leu Arg Arg Glu Gln Met Phe
                245                 250                 255
Val Arg His Leu Phe Asn Arg Ala Gly Ala Val Gly Glu Asn Val Pro
            260                 265                 270
Asp Asp Leu Tyr Ile Lys Gly Ser Gly Ser Thr Ala Asn Leu Ala Ser
            275                 280                 285
Ser Asn Tyr Phe Pro Thr Pro Ser Gly Ser Met Val Thr Ser Asp Ala
            290                 295                 300
Gln Ile Phe Asn Lys Pro Tyr Trp Leu Gln Arg Ala Gln Gly His Asn
305                 310                 315                 320
Asn Gly Ile Cys Trp Gly Asn Gln Leu Phe Val Thr Val Val Asp Thr
                325                 330                 335
Thr Arg Ser Thr Asn Met Ser Leu Cys Ala Ala Ile Ser Thr Ser Glu
            340                 345                 350
Thr Thr Tyr Lys Asn Thr Asn Phe Lys Glu Tyr Leu Arg His Gly Glu
            355                 360                 365
Glu Tyr Asp Leu Gln Phe Ile Phe Gln Leu Cys Lys Ile Thr Leu Thr
            370                 375                 380
Ala Asp Val Met Thr Tyr Ile His Ser Met Asn Ser Thr Ile Leu Glu
385                 390                 395                 400
Asp Trp Asn Phe Gly Leu Gln Pro Pro Pro Gly Gly Thr Leu Glu Asp
                405                 410                 415
Thr Tyr Arg Phe Val Thr Ser Gln Ala Ile Ala Ser Gln Lys His Thr
            420                 425                 430
Pro Pro Ala Pro Lys Glu Asp Pro Leu Lys Lys Tyr Thr Phe Trp Glu
            435                 440                 445
Val Asn Leu Lys Glu Lys Phe Ser Ala Asp Leu Asp Gln Phe Pro Leu
450                 455                 460
Gly Arg Lys Phe Leu Leu Gln Ala Gly Leu Lys Ala Lys Pro Lys Phe
465                 470                 475                 480
Thr Leu Gly Gly Gly Gly Cys Ser Trp Ala Pro Pro Phe Lys Ala Ser
                485                 490                 495
Cys
```

<210> SEQ ID NO 7
<211> LENGTH: 1500
<212> TYPE: DNA
<213> ORGANISM: Artificial Sequence
<220> FEATURE:
<223> OTHER INFORMATION: Description of Artificial Sequence: biotin-binding papillomavirus protein 169
<221> NAME/KEY: CDS
<222> LOCATION: (1)..(1497)

<400> SEQUENCE: 7

```
atg tct ctt tgg ctg cct agt gag gcc act gtc tac ttg cct cct gtc        48
Met Ser Leu Trp Leu Pro Ser Glu Ala Thr Val Tyr Leu Pro Pro Val
 1               5                  10                  15
```

```
cca gta tct aag gtt gta agc acg gat gaa tat gtt gca cgc aca aac    96
Pro Val Ser Lys Val Val Ser Thr Asp Glu Tyr Val Ala Arg Thr Asn
         20                  25                  30 ata tat tat cat gca gga aca tcc aga cta ctt gca gtt gga cat ccc   144
Ile Tyr Tyr His Ala Gly Thr Ser Arg Leu Leu Ala Val Gly His Pro
     35                  40                  45 tat ttt cct att aaa aaa cct aac aat aac aaa ata tta gtt cct aaa   192
Tyr Phe Pro Ile Lys Lys Pro Asn Asn Asn Lys Ile Leu Val Pro Lys
 50                  55                  60 gta tca gga tta caa tac agg gta ttt aga ata cat tta cct gac ccc   240
Val Ser Gly Leu Gln Tyr Arg Val Phe Arg Ile His Leu Pro Asp Pro
 65                  70                  75                  80 aat aag ttt ggt ttt cct gac acc tca ttt tat aat cca gat aca cag   288
Asn Lys Phe Gly Phe Pro Asp Thr Ser Phe Tyr Asn Pro Asp Thr Gln
                 85                  90                  95 cgg ctg gtt tgg gcc tgt gta ggt gtt gag gta ggt cgt ggt cag cca   336
Arg Leu Val Trp Ala Cys Val Gly Val Glu Val Gly Arg Gly Gln Pro
            100                 105                 110 tta ggt gtg ggc att agt ggc cat cct tta tta aat aaa ttg gat gac   384
Leu Gly Val Gly Ile Ser Gly His Pro Leu Leu Asn Lys Leu Asp Asp
        115                 120                 125 aca gaa aat gct agt gct tat gca gca aat gca ggt gtg gat aat aga   432
Thr Glu Asn Ala Ser Ala Tyr Ala Ala Asn Ala Gly Val Asp Asn Arg
    130                 135                 140 gaa tgt ata tct atg gat tac aaa caa aca caa ttg tgt tta att ggt   480
Glu Cys Ile Ser Met Asp Tyr Lys Gln Thr Gln Leu Cys Leu Ile Gly
145                 150                 155                 160 tgc aaa cca cct ata ggg gaa cac tgg ggc aaa gga tcc cca tgt acc   528
Cys Lys Pro Pro Ile Gly Glu His Trp Gly Lys Gly Ser Pro Cys Thr
                165                 170                 175 aat gtt gca gta aat cca ggt gat tgt cca cca tta gag tta ata aac   576
Asn Val Ala Val Asn Pro Gly Asp Cys Pro Pro Leu Glu Leu Ile Asn
            180                 185                 190 aca gtt att cag gat ggt gat atg gtt gat act ggc ttt ggt gct atg   624
Thr Val Ile Gln Asp Gly Asp Met Val Asp Thr Gly Phe Gly Ala Met
        195                 200                 205 gac ttt act aca tta cag gct aac aaa agt gaa gtt cca ctg gat att   672
Asp Phe Thr Thr Leu Gln Ala Asn Lys Ser Glu Val Pro Leu Asp Ile
    210                 215                 220 tgt aca tct att tgc aaa tat cca gat tat att aaa atg gtg tca gaa   720
Cys Thr Ser Ile Cys Lys Tyr Pro Asp Tyr Ile Lys Met Val Ser Glu
225                 230                 235                 240 cca tat ggc gac agc tta ttt ttt tat tta cga agg gaa caa atg ttt   768
Pro Tyr Gly Asp Ser Leu Phe Phe Tyr Leu Arg Arg Glu Gln Met Phe
                245                 250                 255 gtt aga cat tta ttt aat agg gct ggt gct gtt ggt gaa aat gta cca   816
Val Arg His Leu Phe Asn Arg Ala Gly Ala Val Gly Glu Asn Val Pro
            260                 265                 270 gac gat tta tac att aaa ggc tct ggg tct act gca aat tta gcc agt   864
Asp Asp Leu Tyr Ile Lys Gly Ser Gly Ser Thr Ala Asn Leu Ala Ser
        275                 280                 285 tca aat tat ttt cct aca cct agt ggt tct atg gtt acc tct gat gcc   912
Ser Asn Tyr Phe Pro Thr Pro Ser Gly Ser Met Val Thr Ser Asp Ala
    290                 295                 300 caa ata ttc aat aaa cct tat tgg tta caa cga gca cag ggc cac aat   960
Gln Ile Phe Asn Lys Pro Tyr Trp Leu Gln Arg Ala Gln Gly His Asn
305                 310                 315                 320 aat ggc att tgt tgg ggt aac caa cta ttt gtt act gtt gtt gat act  1008
Asn Gly Ile Cys Trp Gly Asn Gln Leu Phe Val Thr Val Val Asp Thr
```

|     |     |     |     |     |     |     |     |     |     |     |     |      |
| --- | --- | --- | --- | --- | --- | --- | --- | --- | --- | --- | --- | ---- |
|     |     |     | 325 |     |     |     | 330 |     |     |     | 335 |      |
| aca | cgc | agt | aca | aat | atg | tca | tta | tgt | gct | gcc | ata | tct act tca gaa | 1056 |
| Thr | Arg | Ser | Thr | Asn | Met | Ser | Leu | Cys | Ala | Ala | Ile | Ser Thr Ser Glu |      |
|     |     |     | 340 |     |     |     | 345 |     |     |     | 350 |      |
| act | aca | tat | aaa | aat | act | aac | ttt | aag | gag | tac | cta | cga cat ggg gag | 1104 |
| Thr | Thr | Tyr | Lys | Asn | Thr | Asn | Phe | Lys | Glu | Tyr | Leu | Arg His Gly Glu |      |
|     |     |     | 355 |     |     |     | 360 |     |     |     | 365 |      |
| gaa | tat | gat | tta | cag | ttt | att | ttt | caa | ctg | tgc | aaa | ata acc tta act | 1152 |
| Glu | Tyr | Asp | Leu | Gln | Phe | Ile | Phe | Gln | Leu | Cys | Lys | Ile Thr Leu Thr |      |
|     | 370 |     |     |     |     | 375 |     |     |     |     | 380 |      |
| gca | gac | gtt | atg | aca | tac | ata | cat | tct | atg | aat | tcc | act att ttg gag | 1200 |
| Ala | Asp | Val | Met | Thr | Tyr | Ile | His | Ser | Met | Asn | Ser | Thr Ile Leu Glu |      |
| 385 |     |     |     |     | 390 |     |     |     |     | 395 |     | 400  |
| gac | tgg | aat | ttt | ggt | cta | caa | cct | ccc | cca | gga | ggc | aca cta gaa gat | 1248 |
| Asp | Trp | Asn | Phe | Gly | Leu | Gln | Pro | Pro | Pro | Gly | Gly | Thr Leu Glu Asp |      |
|     |     |     |     | 405 |     |     |     |     | 410 |     |     | 415  |
| act | tat | agg | ttt | gta | acc | tcc | cag | gca | att | gct | agt | caa aaa cat aca | 1296 |
| Thr | Tyr | Arg | Phe | Val | Thr | Ser | Gln | Ala | Ile | Ala | Ser | Gln Lys His Thr |      |
|     |     |     | 420 |     |     |     |     | 425 |     |     |     | 430  |
| cct | cca | gca | cct | aaa | gaa | gat | ccc | ctt | aaa | aaa | tac | act ttt tgg gaa | 1344 |
| Pro | Pro | Ala | Pro | Lys | Glu | Asp | Pro | Leu | Lys | Lys | Tyr | Thr Phe Trp Glu |      |
|     |     | 435 |     |     |     |     | 440 |     |     |     |     | 445  |
| gta | aat | tta | aag | gaa | aag | ttt | tct | gca | gac | cta | gat | cag ttt cct tta | 1392 |
| Val | Asn | Leu | Lys | Glu | Lys | Phe | Ser | Ala | Asp | Leu | Asp | Gln Phe Pro Leu |      |
|     | 450 |     |     |     |     | 455 |     |     |     |     | 460 |      |
| gga | cgc | aaa | ttt | tta | cta | caa | gca | gga | ttg | aag | gcc | aaa cca aaa ttt | 1440 |
| Gly | Arg | Lys | Phe | Leu | Leu | Gln | Ala | Gly | Leu | Lys | Ala | Lys Pro Lys Phe |      |
| 465 |     |     |     | 470 |     |     |     |     | 475 |     |     | 480  |
| aca | tta | gga | ggc | ggc | ggc | cgc | ggc | gag | ttc | acc | ggc | acc tac atc acc | 1488 |
| Thr | Leu | Gly | Gly | Gly | Gly | Arg | Gly | Glu | Phe | Thr | Gly | Thr Tyr Ile Thr |      |
|     |     |     |     | 485 |     |     |     |     | 490 |     |     | 495  |
| gcc | gtg | acc | taa |     |     |     |     |     |     |     |     | 1500 |
| Ala | Val | Thr |     |     |     |     |     |     |     |     |     |      |

<210> SEQ ID NO 8
<211> LENGTH: 499
<212> TYPE: PRT
<213> ORGANISM: Artificial Sequence
<220> FEATURE:
<223> OTHER INFORMATION: Description of Artificial Sequence:
      biotin-binding papillomavirus protein 169

<400> SEQUENCE: 8

Met Ser Leu Trp Leu Pro Ser Glu Ala Thr Val Tyr Leu Pro Pro Val
 1               5                  10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

-continued

```
Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
            165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
            195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
            245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
            275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
            325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
    355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
            405                 410                 415

Thr Tyr Arg Phe Val Thr Ser Gln Ala Ile Ala Ser Gln Lys His Thr
            420                 425                 430

Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Gly Gly Gly Arg Gly Glu Phe Thr Gly Thr Tyr Ile Thr
            485                 490                 495

Ala Val Thr
```